US008369938B2

(12) United States Patent
Dong et al.

(10) Patent No.: US 8,369,938 B2
(45) Date of Patent: Feb. 5, 2013

(54) RHYTHM DISCRIMINATION ENHANCEMENT—CHAMBER OF TACHY ORIGINATION

(75) Inventors: Yanting Dong, Shoreview, MN (US); Deepa Mahajan, Circle Pines, MN (US); David L. Perschbacher, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 9 days.

(21) Appl. No.: 13/196,469

(22) Filed: Aug. 2, 2011

(65) Prior Publication Data
US 2012/0035489 A1 Feb. 9, 2012

Related U.S. Application Data

(60) Provisional application No. 61/371,383, filed on Aug. 6, 2010.

(51) Int. Cl.
*A61B 5/04* (2006.01)
(52) U.S. Cl. ....................................................... 600/516
(58) Field of Classification Search .................. 600/516
See application file for complete search history.

(56) References Cited

U.S. PATENT DOCUMENTS

| | | | |
|---|---|---|---|
| 4,872,459 A | 10/1989 | Pless et al. | |
| 4,880,005 A | 11/1989 | Pless et al. | |
| 5,814,085 A | 9/1998 | Hill | |
| 6,058,328 A | 5/2000 | Levine et al. | |
| 6,314,321 B1 | 11/2001 | Morris | |
| 6,477,420 B1 * | 11/2002 | Struble et al. | 607/14 |
| 6,493,579 B1 | 12/2002 | Gilkerson et al. | |
| 6,567,691 B1 | 5/2003 | Stadler | |
| 6,636,764 B1 | 10/2003 | Fain et al. | |
| 6,681,134 B2 | 1/2004 | Morris et al. | |
| 6,708,058 B2 | 3/2004 | Kim et al. | |
| 6,889,079 B2 | 5/2005 | Bocek et al. | |
| 7,031,764 B2 | 4/2006 | Schwartz et al. | |
| 7,050,852 B2 | 5/2006 | Zhu et al. | |
| 7,162,300 B2 | 1/2007 | van Groeningen et al. | |
| 7,203,538 B2 | 4/2007 | Schwartz et al. | |
| 7,212,855 B1 | 5/2007 | Kroll et al. | |

(Continued)

FOREIGN PATENT DOCUMENTS

WO WO-2007133762 A1 11/2007

OTHER PUBLICATIONS

Aliot, Etienne, et al., "Arrhythmia detection by dual-chamber implantable cardioverter defibrillators. A review of current algorithms", Europace, 6(4), (Jul. 2004), 273-86.

(Continued)

*Primary Examiner* — George Manuel
(74) *Attorney, Agent, or Firm* — Schwegman Lundberg & Woessner, P.A.

(57) ABSTRACT

An apparatus comprises an implantable cardiac signal sensing circuit and a controller circuit. The implantable cardiac signal sensing circuit provides a sensed depolarization signal from a ventricle and a sensed depolarization signal from an atrium. The controller circuit includes an onset detection circuit and a classification circuit. The onset detection circuit detects an onset episode that includes fast cardiac depolarizations and identifies a depolarization that initiates the onset episode. The classification circuit classifies the onset episode as supra-ventricular tachycardia (SVT) when the initiating onset episode is identified in the atrium and the number of atrial depolarizations is greater than or equal to the number of ventricular depolarizations during the onset episode, and as ventricular tachycardia (VT) when the initiating onset depolarization is identified in the ventricle and the number of ventricular depolarizations is greater than the number of atrial depolarizations during the onset episode.

20 Claims, 11 Drawing Sheets

U.S. PATENT DOCUMENTS

| | | |
|---|---|---|
| 7,225,020 B1 | 5/2007 | Kroll et al. |
| 7,313,436 B2 | 12/2007 | Hess |
| 7,321,794 B2 | 1/2008 | Thacker et al. |
| 7,346,388 B2 | 3/2008 | Elahi et al. |
| 7,363,081 B1 | 4/2008 | Kroll et al. |
| 7,440,799 B2 | 10/2008 | Morris |
| 7,537,569 B2 | 5/2009 | Sarkar et al. |
| 7,664,553 B2 | 2/2010 | Roberts |
| 2006/0287684 A1 | 12/2006 | Baynham et al. |
| 2007/0049835 A1 | 3/2007 | Goode |
| 2007/0135852 A1 | 6/2007 | Kim et al. |
| 2007/0167987 A1 | 7/2007 | Schwartz et al. |
| 2007/0197928 A1 | 8/2007 | Kim et al. |
| 2008/0281370 A1 | 11/2008 | Lin et al. |
| 2009/0118781 A1 | 5/2009 | Morris |
| 2009/0264716 A1 | 10/2009 | Shuros et al. |

OTHER PUBLICATIONS

Keung, Edward, "SVT Discrimination Algorithm", San Francisco VA Hospital, (Jan. 23, 2009), 19 pgs.

Swerdlow, C. D, et al., "Advanced ICD troubleshooting: Part I.", Pacing Clin Electrophysiol., 28(12), (Dec. 2005), 1322-46.

* cited by examiner

RHYTHM DISCRIMINATION ENHANCEMENT—CHAMBER OF TACHY ORIGINATION

CROSS-REFERENCE TO RELATED APPLICATIONS

This application claims the benefit of U.S. Provisional Application No. 61/371,383, filed on Aug. 6, 2010, under 35 U.S.C. §119(e), which is incorporated herein by reference in its entirety.

BACKGROUND

Implantable medical devices (IMDs) include devices designed to be implanted into a patient. Some examples of these devices include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of implantable medical devices include implantable diagnostic devices, implantable drug delivery systems, or implantable devices with neural stimulation capability.

Additionally, some IMDs detect events by monitoring electrical heart activity signals. In CFM devices, these events can include heart chamber expansions or contractions. By monitoring cardiac signals indicative of expansions or contractions, IMDs can detect abnormally slow heart rate, or bradycardia. Some IMDs detect abnormally rapid heart rate, or tachyarrhythmia. Tachyarrhythmia includes ventricular tachycardia (VT). Tachyarrhythmia also includes rapid and irregular heart rate, or fibrillation, including ventricular fibrillation (VF).

Tachyarrhythmia also includes supraventricular tachycardia (SVT). SVT is less dangerous to the patient than VT or VF. SVT includes arrhythmias such as atrial tachycardia, atrial flutter, and atrial fibrillation. A rapid heart rate can also be due to sinus tachycardia (ST), which is a normal response to, for example, exercise or an elevated emotional state. When detected, tachyarrhythmia can be terminated with high-energy shock therapy delivered with an ICD. It is important for cardioverter defibrillators to quickly and accurately classify sensed rhythms or arrhythmias and deliver the appropriate therapy.

OVERVIEW

This document relates generally to systems, devices, and methods for monitoring cardiac electrophysiological parameters of a patient or subject. Episodes of atrial and ventricular tachyarrhythmia are also monitored.

Example 1 includes subject matter (such as an apparatus) comprising an implantable cardiac signal sensing circuit and a controller circuit. The implantable cardiac signal sensing circuit provides a sensed depolarization signal from a ventricle and a sensed depolarization signal from an atrium. The controller circuit includes an onset detection circuit and a classification circuit. The onset detection circuit detects an onset episode that includes fast cardiac depolarizations and identifies a depolarization that initiates the onset episode. The classification circuit classifies the onset episode as supraventricular tachycardia (SVT) when the V-V intervals differ from the A-A intervals by less than a specified interval threshold during the onset episode, the initiating onset depolarization is identified in the atrium, and the number of atrial depolarizations is greater than or equal to the number of ventricular depolarizations during the onset episode. The classification circuit classifies the episode as ventricular tachycardia (VT) when the V-V intervals differ from the A-A intervals by less than a specified interval threshold during the onset episode, the initiating onset depolarization is identified in the ventricle, and the number of ventricular depolarizations is greater than the number of atrial depolarizations during the onset episode. The classification circuit provides the classification to a user or process.

In Example 2, the onset detection circuit of Example 1 can optionally be configured to detect a premature ventricular contraction (PVC), and the classification circuit can optionally be configured to classify the onset as VT when: the V-V intervals and the A-A intervals differ by less than a specified interval threshold during the onset episode, the onset episode begins in the ventricle, the number of ventricular depolarizations is greater than the number of atrial depolarizations during the onset episode, and a PVC is detected near a ventricular depolarization designated as start of the onset episode.

In Example 3, the onset detection circuit of one or any combination of Examples 2 and 3 can optionally be configured to: identify two ventricular depolarizations that occur, without an intervening atrial beat, within N beats of the designated ventricular onset depolarization, wherein N is an integer, and provide an indication that a PVC has occurred when detecting less than two atrial depolarizations during two ventricular depolarizations following the two identified ventricular depolarizations.

In Example 4, the onset detection circuit of one or any combination of Examples 1-3 can optionally be configured to provide an indication that a PVC has occurred when detecting an atrio-ventricular (AV) interval that is less than a specified threshold AV interval within N cardiac cycles of the ventricular onset depolarization, wherein N is an integer.

In Example 5, the onset detection circuit of one or any combination of Examples 1-4 can optionally be configured to identify an onset cardiac depolarization in the atrium and an onset cardiac depolarization in the ventricle, and the classification circuit can optionally be configured to determine that the onset is initiated in the atrium when the atrial onset depolarization occurs before the ventricular onset depolarization and no PVCs are detected near the identified ventricular onset depolarization.

In Example 6, the onset detection circuit of one or any combination of Examples 1-5 can optionally be configured to: determine a threshold onset interval value using sensed cardiac depolarizations, identify a depolarization as a candidate onset depolarization if the depolarization completes an interval less than the threshold onset interval value, and classify the candidate onset depolarization as an initiating onset depolarization when X depolarization intervals of the next Y cardiac depolarizations following the candidate onset depolarization are less than the threshold onset interval value, wherein X and Y are positive integers and X is less than Y.

In Example 7, the onset detection circuit of one or any combination of Examples 1-6 can optionally be configured to calculate a statistical metric of a depolarization interval change measured over a specified number of previous depolarization intervals, and determine the threshold onset interval value using the statistical metric.

In Example 8 the subject matter of Example 7 optionally includes a storage circuit communicatively coupled to the controller and configured to store a look-up table of threshold onset interval values, and the onset detection circuit can optionally be configured to determine the threshold onset value from the look-up table using the calculated statistical metric.

In Example 9, the onset detection circuit of one or any combination of Examples 1-8 can optionally be configured to: identify more than one candidate onset interval within the Y beats as the onset interval, select the first identified onset interval as the confirmed onset interval when the candidate onset intervals are consecutive, and select the second identified onset interval as the confirmed onset interval when the candidate onset intervals are non-consecutive.

In Example 10, the subject matter of one or any combination of Examples 1-9 optionally includes a storage circuit communicatively coupled to, or integral to, the controller circuit. The controller circuit can optionally be configured to store a segment of the atrial depolarization signal and a segment of the ventricular depolarization signal using the storage circuit when the onset episode is detected, and the classification circuit can optionally be configured to classify the onset episode using the stored signal segments when the onset is detected.

In Example 11, the onset detection circuit of one or any combination of Examples 1-10 can optionally be configured to count the number of depolarizations during the onset episode until the onset is classified, and restart the count if a new onset episode is detected before the before the onset episode is classified.

Example 12 can include, or can optionally be combined with the subject matter of one or any combination of Examples 1-11 to include, subject matter (such as a method, a means for performing acts, or a machine readable medium including instructions that, when performed by the machine, cause the machine to perform acts) comprising sensing cardiac depolarizations in an atrium and in a ventricle of a heart of a subject using an implantable medical device (IMD), detecting an onset episode that includes fast cardiac depolarizations, determining that ventricular depolarization intervals (V-V intervals) and atrial depolarization intervals (A-A intervals) differ by less than a specified interval threshold during the onset episode, identifying a depolarization that initiates the onset episode, classifying the onset episode as supraventricular tachycardia (SVT) when the initiating onset depolarization is identified in the atrium and the number of atrial depolarizations is greater than or equal to the number of ventricular depolarizations during the onset episode, classifying the onset episode as ventricular tachycardia (VT) when the initiating onset depolarization is identified in the ventricle and the number of ventricular depolarizations is greater than the number of atrial depolarizations during the onset episode, and providing the classification to a user or process.

In Example 13, the classifying the onset of Example 12 optionally includes classifying the onset episode as VT when: determining that the V-V intervals differ from A-A intervals by less than the specified interval threshold during the onset episode, determining that the onset episode begins in the ventricle, determining that the number of ventricular depolarizations is greater than the number of atrial depolarizations during the onset episode, and detecting a premature ventricular contraction (PVC) near a ventricular depolarization designated as start of the onset episode.

In Example 14, the detecting a PVC of Example 13 optionally includes identifying two ventricular depolarizations, that occur without an intervening atrial depolarization, within N cardiac cycles of the ventricular onset depolarization, wherein N is an integer, and deeming a PVC has occurred when detecting less than two atrial depolarizations during two ventricular depolarizations following the two identified ventricular depolarizations.

In Example 15, the detecting a PVC of one or any combination of Examples 13 and 14 optionally includes detecting an atrio-ventricular (AV) interval that is less than a specified threshold AV interval within N cardiac cycles of the ventricular onset depolarization, wherein N is an integer.

In Example 16, the subject matter of one or any combination of Examples 12-15 optionally includes identifying an onset cardiac depolarization in the atrium and an onset cardiac depolarization in the ventricle, and deeming that the onset is initiated in the atrium when the identified atrial onset depolarization occurs within a specified time duration before the identified ventricular onset depolarization and no PVCs are detected near the identified ventricular onset depolarization.

In Example 17, the detecting the onset of fast cardiac depolarizations of one or any combination of Examples 12-16 optionally includes determining a threshold onset interval value, identifying a depolarization as a candidate onset depolarization if the depolarization completes an interval less than the threshold onset interval value, and confirming the candidate onset depolarization as an initiating onset interval when X depolarization intervals of the next Y cardiac depolarizations following the candidate onset depolarization complete intervals less than the threshold onset interval value, wherein X and Y are positive integers and X is less than Y.

In Example 18, the determining a threshold onset interval value of Example 17 optionally includes determining the threshold onset interval value by applying a statistical metric to a depolarization interval change measured over a specified number of previous depolarization intervals.

In Example 19, the confirming the onset interval of one or any combination of Examples 17 and 18 optionally includes, when identifying more than one candidate onset interval within the Y beats as the onset interval, selecting the first identified onset interval as the confirmed onset interval when the candidate onset intervals are consecutive, and selecting the second identified onset interval as the confirmed onset interval when the candidate onset intervals are non-consecutive.

In Example 20, the subject matter of one or any combination of Examples 12-19 optionally includes classifying the onset episode as one of VT or SVT when a determined ventricular depolarization rate differs from a determined atrial depolarization rate by less than a specified rate threshold.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This document discusses systems and methods for improved detection of cardiac events by an IMD. Specifically systems and methods for improved discrimination or classification of tachyarrhythmia by an IMD are described.

An implantable medical device (IMD) may include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions.

Figure 1:
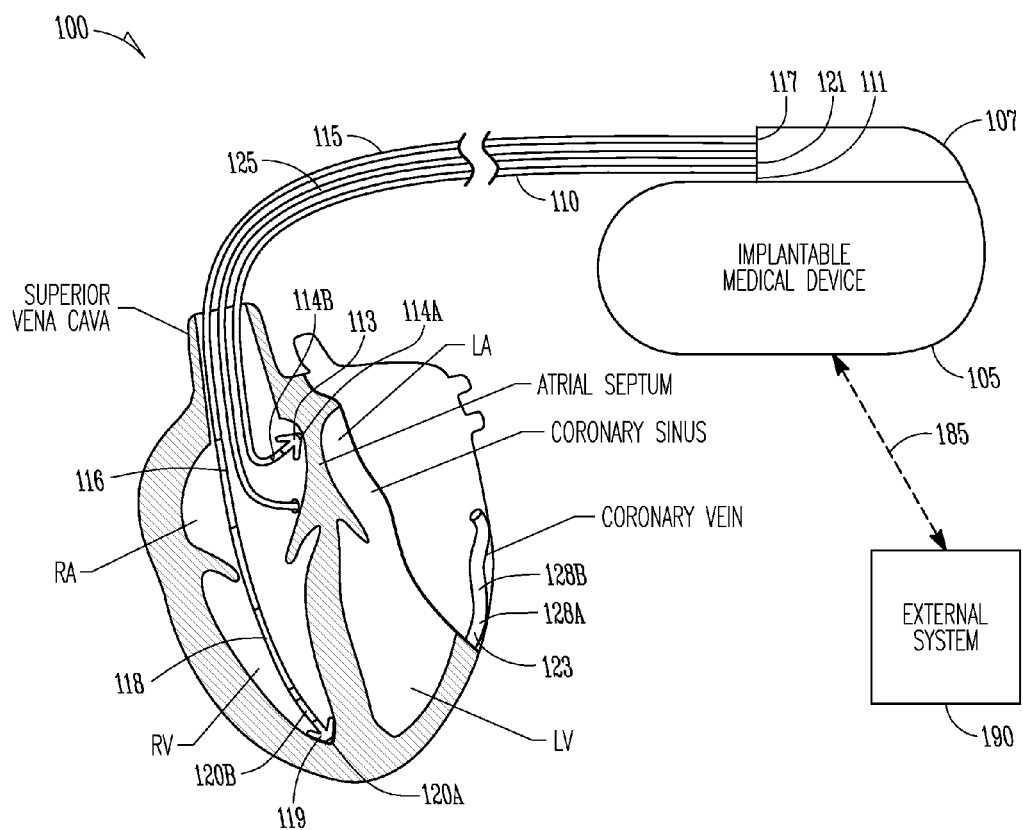
FIG. 1 is an illustration of portions of a system that uses an IMD.

FIG. 1 is an illustration of portions of a system 100 that uses an IMD 105. Examples of the IMD 105 include, without limitation, a pacemaker, a cardioverter, a defibrillator, a cardiac resynchronization therapy (CRT) device, and other cardiac monitoring and therapy delivery devices, including cardiac devices that include or work in coordination with one or more neuro-stimulating devices, drugs, drug delivery systems, or other therapies. As one example, the system 100 shown can be used to detect and treat a cardiac arrhythmia such as tachyarrhythmia. The IMD 105 typically includes an electronics unit coupled by one or more cardiac leads 110, 115, 125, to a heart of a patient or subject. The electronics unit of the IMD 105 typically includes components that are enclosed in a hermetically-sealed housing or "can." System 100 also typically includes an IMD programmer or other external system 190 that communicates one or more wireless signals 185 with the IMD 105, such as by using radio frequency (RF) or one or more other telemetry signals.

The example shown includes right atrial (RA) lead 110 having a proximal end 111 and a distal end 113. Proximal end 111 is coupled to a header connector 107 of the IMD 105. Distal end 113 is configured for placement in the RA in or near the atrial septum. RA lead 110 may include a pair of bipolar electrodes, such as an RA tip electrode 114A and an RA ring electrode 114B. RA electrodes 114A and 114B are incorporated into the lead body at distal end 113 for placement in or near the atrial septum, and are each electrically coupled to IMD 105 through a conductor extending within the lead body. The RA lead is shown placed in or near the atrial septum, but the RA lead may be placed in the atrial appendage.

The example shown also includes right ventricular (RV) lead 115 having a proximal end 117 and a distal end 119. Proximal end 117 is coupled to header connector 107. Distal end 119 is configured for placement in the RV. RV lead 115 may include one or more of a proximal defibrillation electrode 116, a distal defibrillation electrode 118, an RV tip electrode 120A, and an RV ring electrode 120B. Defibrillation electrode 116 is incorporated into the lead body in a location suitable for supraventricular placement in the RA or the superior vena cava. Defibrillation electrode 118 is incorporated into the lead body near distal end 119 for placement in the RV. RV electrodes 120A and 120B may form a bipolar electrode pair and are incorporated into the lead body at distal end 119. Electrodes 116, 118, 120A, and 120B are each electrically coupled to IMD 105 through a conductor extending within the lead body. Proximal defibrillation electrode 116, distal defibrillation electrode 118, and/or an electrode formed on the can of IMD 105 allow for delivery of cardioversion/defibrillation pulses to the heart.

RV tip electrode 120A, RV ring electrode 120B, and/or an electrode formed on the can of IMD 105 allow for sensing an RV electrogram indicative of RV depolarizations and delivering RV pacing pulses. Any combination of RV tip electrode 120A, RV ring electrode 120B, and an electrode formed on the can of IMD 105, or other ventricular electrode can be referred to as a ventricular channel. RA tip electrode 114A, RA ring electrode 114B, and/or an electrode formed on the can of IMD 105 allow for sensing an RA electrogram indicative of RA depolarizations and delivering RA pacing pulses. Any combination of RA tip electrode 114A, RA ring electrode 114B, electrode formed on the can of IMD 105, and/or other atrial electrode can be referred to as an atrial channel. Sensing channels can also include defibrillation electrodes. Any combination of electrodes that includes the proximal defibrillation electrode 116, the distal defibrillation electrode 118, and/or an electrode formed on the can of the IMD 105 can be referred to as a shock channel.

Sensing and pacing allows the IMD 105 to adjust timing of the heart chamber contractions. In some device examples, IMD 105 can adjust the timing of ventricular contractions with respect to the timing of atrial contractions delay by sensing a contraction in the RA and pacing the RV at the desired atrial-ventricular (AV) delay time.

Also shown is a left ventricular (LV) lead 125. LV lead 125 is a coronary pacing and/or sensing lead that includes an elongate lead body having a proximal end 121 and a distal end 123. Proximal end 121 is coupled to header connector 107. Distal end 123 is configured for placement or insertion in the coronary vein. LV lead 125 may include an LV ring or tip electrode 128A and an LV ring electrode 128B. The distal portion of LV lead 125 is configured for placement in the coronary sinus and coronary vein such that LV electrodes 128A and 128B are placed in the coronary vein. LV electrodes 128A and 128B may form a bipolar electrode pair and are incorporated into the lead body at distal end 123 and each electrically coupled to IMD 105 through a conductor extending within the lead body. LV tip electrode 128A, LV ring electrode 128B, and/or an electrode formed on the can of IMD 105 allow for sensing an LV electrogram indicative of LV depolarizations and delivering LV pacing pulses. Any combination of LV tip electrode 128A, LV ring electrode 128B, and/or electrode formed on the can of IMD 105, and/or other ventricular electrode can also be referred to as a ventricular channel.

Other forms of electrodes include meshes and patches, which may be applied to one or more portions of heart, or which may be implanted in one or more other areas of the body to help "steer" electrical current produced by IMD 105 in FIG. 1. The IMDs may be configured with a variety of electrode arrangements, including transvenous, endocardial, or epicardial electrodes (e.g., intrathoracic electrodes), or subcutaneous, non-intrathoracic electrodes, such as can, header, or indifferent electrodes, or subcutaneous array or lead electrodes (e.g., non-intrathoracic electrodes). Monitoring of electrical signals related to cardiac activity may provide early, if not immediate, diagnosis of cardiac disease.

Typically, cardioverter defibrillators detect tachyarrhythmia by first detecting a rapid heart rate. Detection enhancements are sometime used to further distinguish or classify the detected arrhythmia. An example includes determining whether the rate detected in a ventricle (V rate) is greater than the rate detected in an atrium (A rate) by a specified rate threshold (e.g., V rate>A rate by more than ten beats per minute, or 10 bpm). This is often an indication that the arrhythmia is VT. However, sometimes the enhancements fail to accurately distinguish VT from SVT, especially during a tachyarrhythmia episode when ventricular events occur about one-to-one with atrial events during the tachyarrhythmia episode.

In some examples, ventricular events are deemed to occur about one-to-one with atrial events during a tachyarrhythmia episode when the detected V rate differs from the detected A rate by less than 10 bpm. In some examples, ventricular events are deemed to occur about one-to-one with atrial events during the tachyarrhythmia episode when the number of ventricular depolarizations differs from the number of atrial depolarizations by two or less depolarizations during the arrhythmia episode. In some examples, ventricular events are deemed to occur about one-to-one with atrial events during the tachyarrhythmia episode when measured ventricular-to-ventricular (V-V) intervals differ from detected atrial-to-atrial (A-A) intervals by less than a specified interval threshold during the onset episode.

To improve classification of detected tachyarrhythmia, determining in which heart chamber the arrhythmia began can improve detection and discrimination of tachyarrhythmia.

Figure 2:
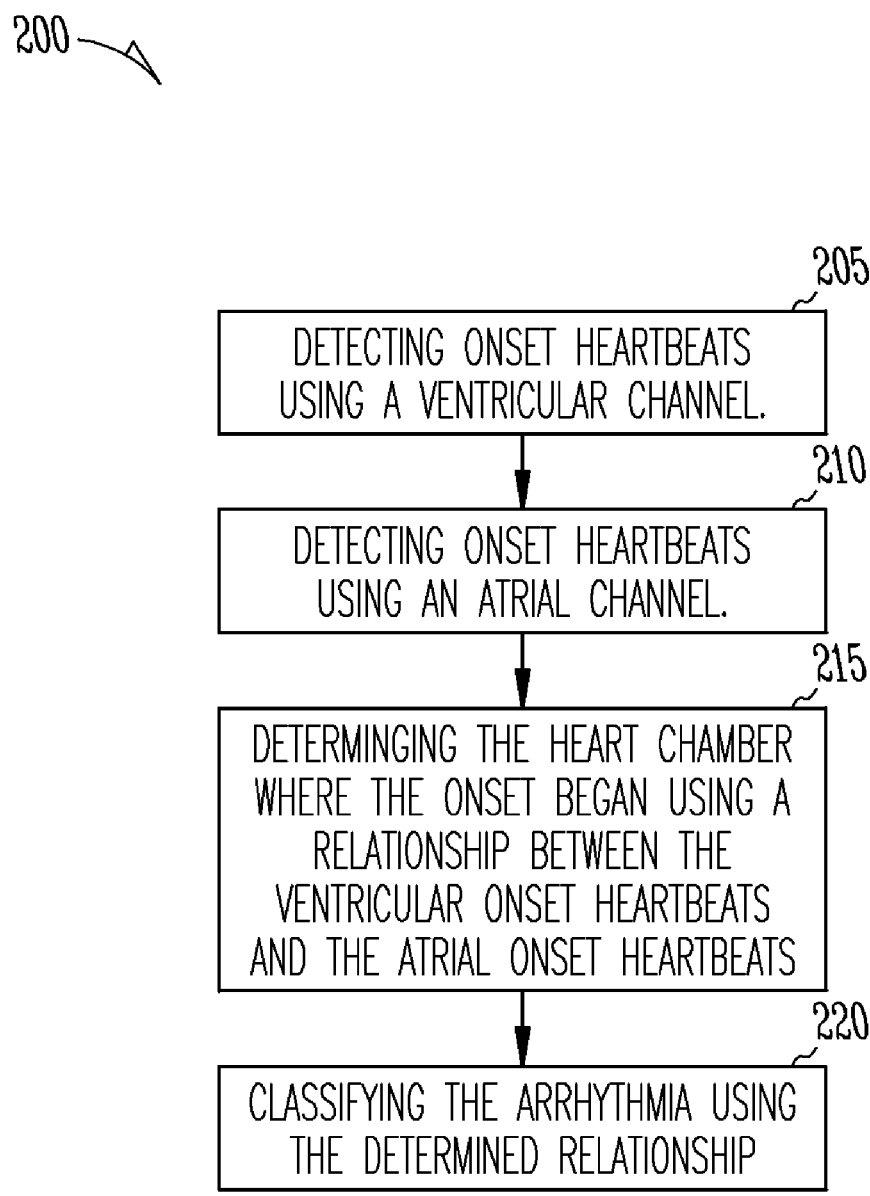
FIG. 2 is a flow chart of an example of a method of classifying a detected tachyarrhythmia.

FIG. 2 is a flow chart of an example of a method 200 of classifying a detected tachyarrhythmia. At block 205, onset heartbeats are detected using a ventricular channel. Onset refers to an onset episode of tachyarrhythmia. In some examples, the onset heartbeats are identified by a ventricular rate that exceeds a specified tachyarrhythmia detection rate threshold. At block 210, onset heartbeats are detected using an atrial channel. At block 215, the heart chamber where the onset began is determined based on a relationship between the onset heartbeats in the ventricle and the onset heartbeats in the atrium.

At block 220, the tachyarrhythmia is classified using the determined relationship. For example, if it is determined that the onset episode began in the atrium, then the tachyarrhythmia is more likely to be SVT. If it is determined that the onset episode began in the ventricle, then the tachyarrhythmia is more likely to be VT.

Figure 3:
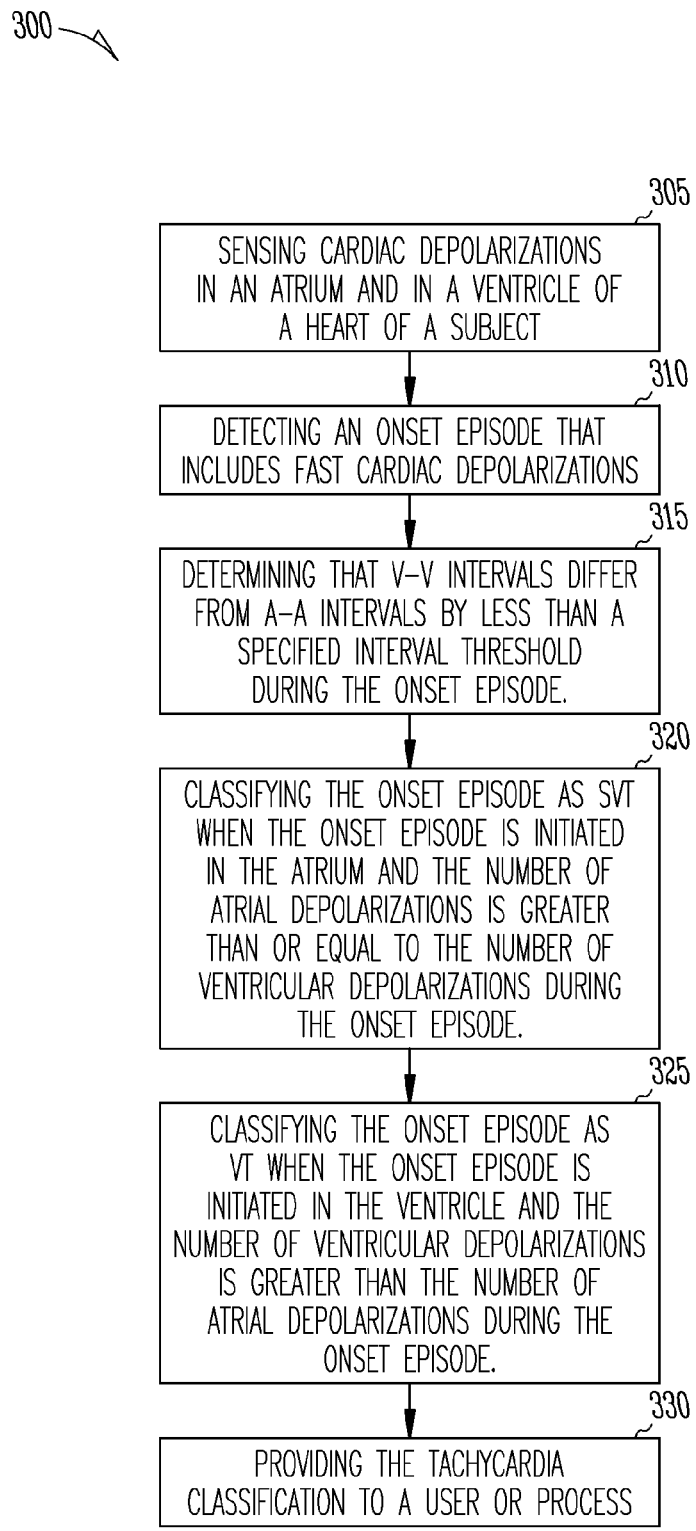
FIG. 3 is a flow chart of another example of a method of classifying a detected tachyarrhythmia.

FIG. 3 is a flow chart of another example of a method 300 of classifying a detected tachyarrhythmia. At block 305, cardiac depolarizations are sensed in an atrium and in a ventricle of a subject using an IMD.

At block 310, a tachyarrhythmia onset episode is detected that includes fast cardiac depolarizations. In some examples, the tachyarrhythmia onset episode is detected when detecting a number of ventricular depolarization intervals that are less than a specified tachyarrhythmia detection interval threshold value.

At block 315, it is determined whether ventricular events occur at about a one-to-one with atrial events during the onset episode. In some examples, this is determined when ventricular depolarization intervals (V-V intervals) differ from atrial depolarization intervals (A-A intervals) by less than a specified interval threshold value during the onset episode.

The chamber where the onset originated is identified. In some examples, the depolarization that initiated the onset episode in the atrium is identified and the depolarization that initiated the onset episode in the ventricle is identified. If the atrial onset depolarization occurred before the ventricular onset depolarization, then the onset episode is deemed to have originated in the atrium. If the ventricular onset depolarization occurred before the atrial onset depolarization, then the onset episode is deemed to have originated in the ventricle.

To identify the onset depolarization in one or both of the atrium and the ventricle, a statistical metric for changes in the depolarization intervals is calculated for a specified number of intervals prior to the detected onset. In some examples, the statistical metric is a standard deviation of the change in the intervals. In certain examples, the standard deviation is calculated over five intervals.

A threshold onset interval value is then determined based on the statistical metric. In some examples, one threshold onset interval is determined for both chambers. In some examples, a threshold onset interval is determined for each heart chamber using a statistical metric calculated for each heart chamber. The onset depolarization may be identified as the first candidate depolarization that completes an interval less than the determined threshold onset interval, and at least X of the next Y (e.g., 2 of 5) intervals that follow the candidate depolarization are also less than the threshold onset interval, where X and Y are positive integers.

Figure 4:
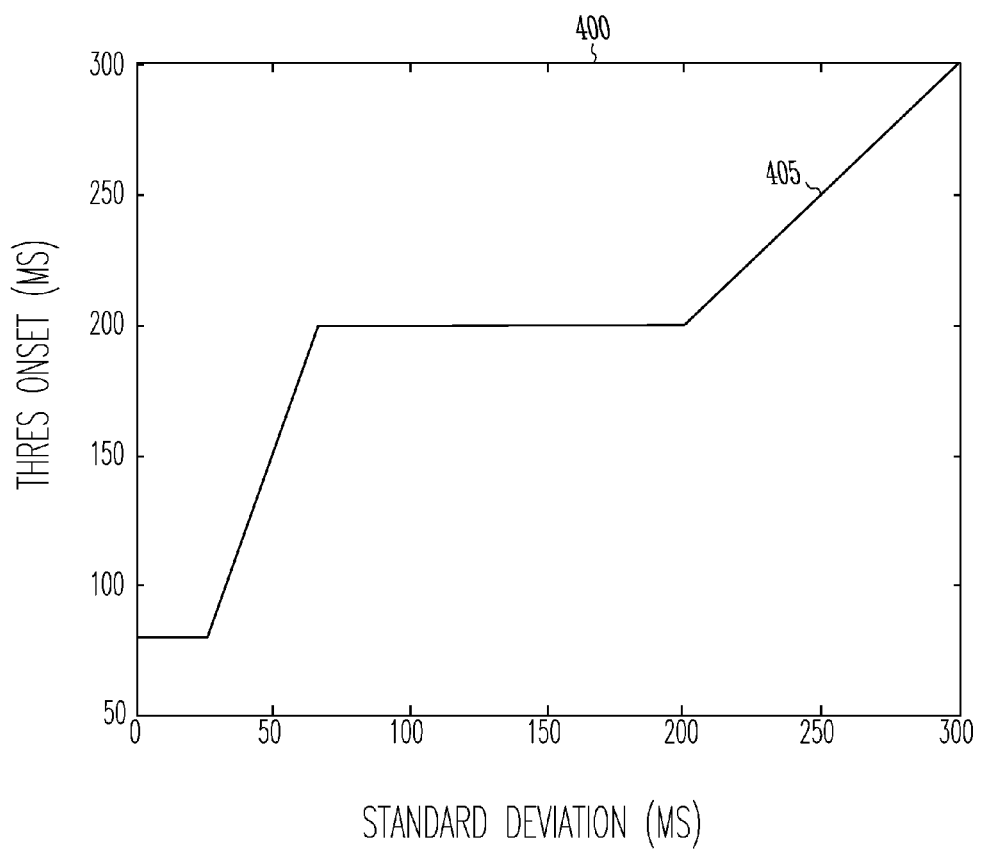
FIG. 4 shows an example of a graph used to determine a threshold onset interval.

FIG. 4 shows an example of a graph 400 used to determine a threshold onset interval. In the example, the statistical metric is the standard deviation and the plot 405 in the graph maps a calculated standard deviation of depolarization intervals to a threshold onset interval value used to identify an onset depolarization. The relationship of the threshold onset intervals to the standard deviations in the Figure was determined using empirical data from recorded episodes of tachyarrhythmia.

Returning to FIG. 3, the detected tachyarrhythmia can be classified when the onset depolarizations are identified. Identifying the onset depolarization in the atrium and the onset depolarization in the ventricle allows determining which onset depolarization happened first and thereby identifies the heart chamber in which the onset episode began.

At block 320, the onset episode is classified as SVT when the onset episode is initiated in the atrium and the number of atrial depolarizations is greater than or equal to the number of ventricular depolarizations during the onset episode. Because the episode is about one-to-one, the difference between the number of atrial onset depolarizations and the number of ventricular onset depolarizations during the episode will be small. Typically there will be about one or two more atrial onset depolarizations than ventricular onset depolarizations when the onset episode begins in the atrium.

Figure 5:
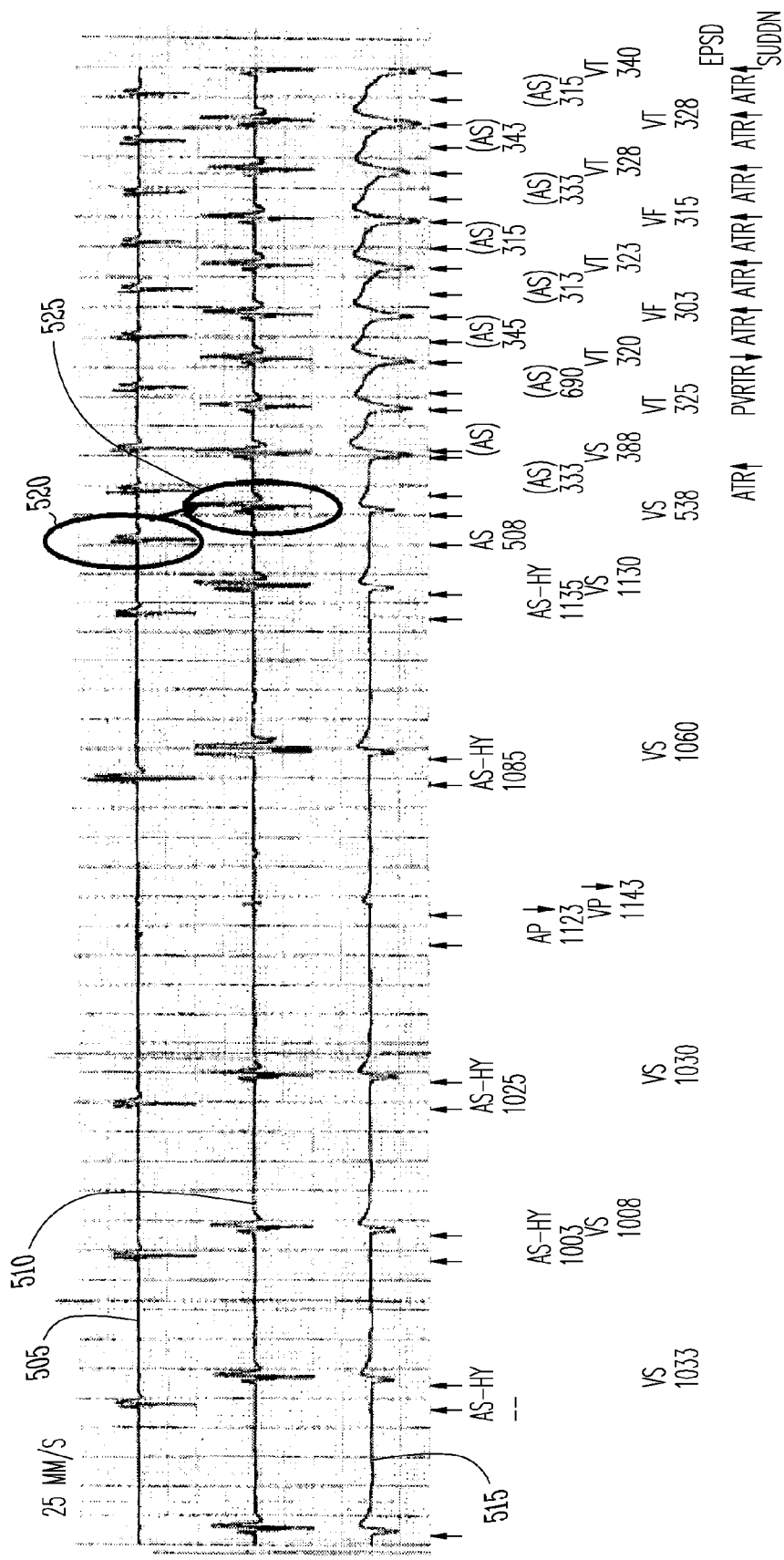
FIG. 5 shows an example of electrograms sensed during a tachyarrhythmia onset episode.

FIG. 5 shows an example of electrograms sensed during a tachyarrhythmia onset episode. The top trace 505 is an electrogram sensed using an atrial channel. The middle trace 510 is an electrogram sensed using a ventricular channel, and the bottom trace 515 is an electrogram sensed using a shock channel. The electrograms show an identified atrial onset depolarization 520 and a ventricular onset depolarization 525. Because the atrial onset depolarization happened earlier, the tachyarrhythmia is classified as SVT. Note that the ventricular events occur at about one-to-one with the atrial events during the episode.

Returning to FIG. 3, at block 325 the onset episode is classified as VT when the onset episode is initiated in the ventricle and the number of ventricular depolarizations is greater than the number of atrial depolarizations during the onset episode.

Figure 6:
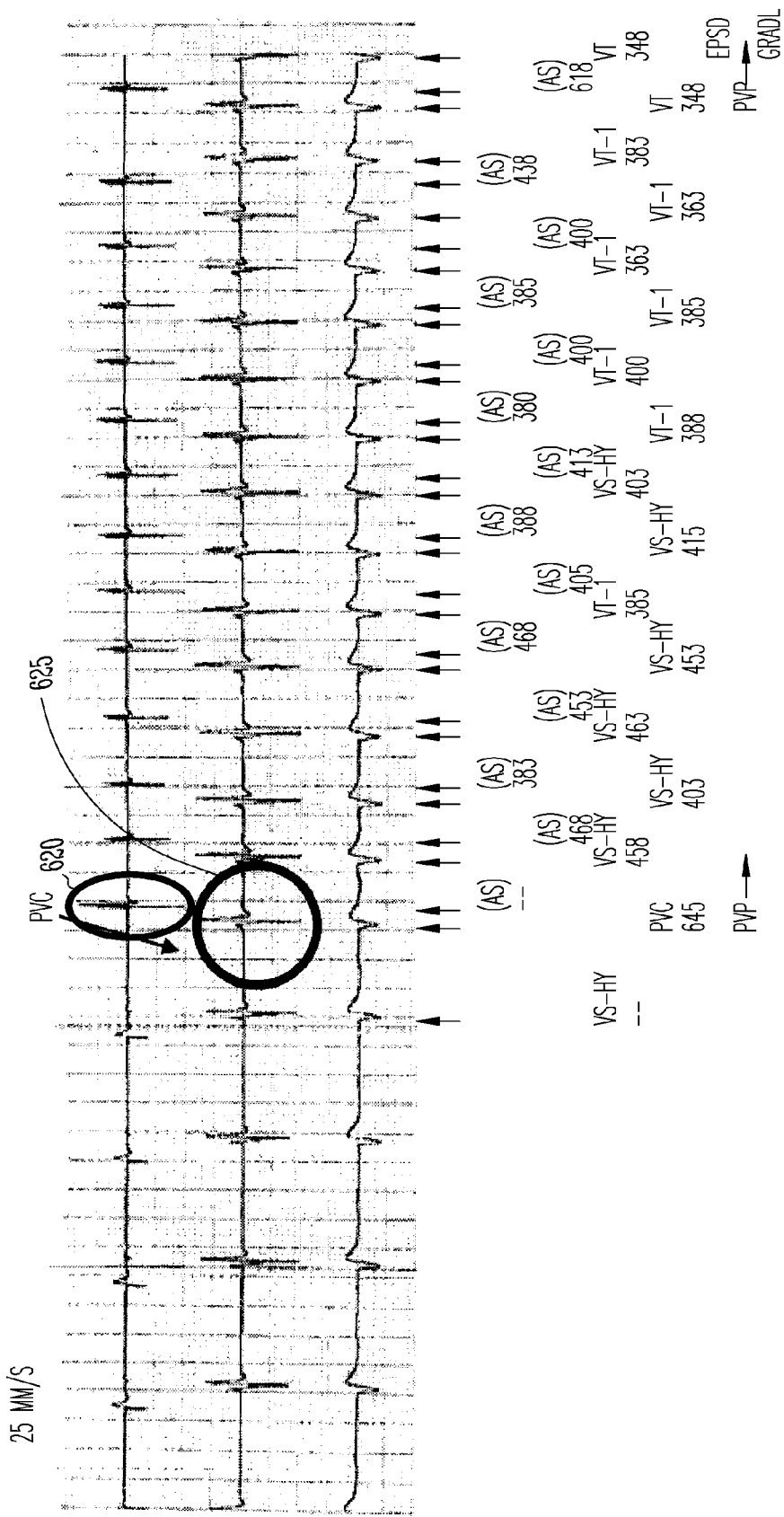
FIG. 6 shows another example of electrograms sensed during a tachyarrhythmia onset episode.

FIG. 6 shows another example of electrograms sensed during a tachyarrhythmia onset episode. The electrograms show an identified atrial onset depolarization 620 and a ventricular onset depolarization 625. Because the ventricular onset depolarization happened earlier than the atrial onset depolarization, the tachyarrhythmia is classified as VT. Note that the ventricular events also occur at about one-to-one with the atrial events during the episode.

Returning to FIG. 3, once the classification of the tachyarrhythmia is made, at block 330 the tachyarrhythmia classification is provided to a user or process. The classification can be provided to a device process to initiate therapy. Because SVT is a less serious arrhythmia than VT, in some examples the device may try to convert the tachyarrhythmia with anti-tachyarrhythmia pacing (ATP) rather than shock therapy when the onset episode is classified as SVT. In certain examples, the device inhibits therapy when the classification is SVT. In some examples, the device may communicate the classification to a second device with a display so that a user can be notified of the classification.

Figure 7:
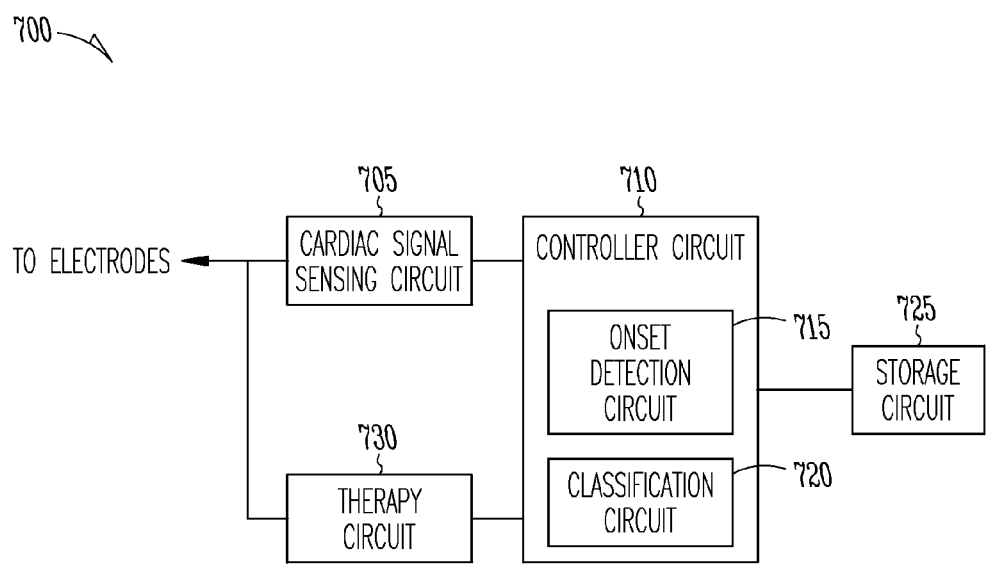
FIG. 7 is a block diagram of portions of an example of a device to classify a detected tachyarrhythmia.

FIG. 7 is a block diagram of portions of an example of a device 700 to classify a detected tachyarrhythmia. The device 700 includes an implantable cardiac signal sensing circuit 705. The cardiac signal sensing circuit 705 provides a sensed depolarization signal from a ventricle and a sensed depolarization signal from an atrium when attached to appropriate electrodes.

The device 700 also includes a controller circuit 710 communicatively coupled to the cardiac signal sensing circuit 705. The communicative coupling allows electrical signals to be communicated between the cardiac signal sensing circuit 705 and the controller circuit 710 even though there may be intervening circuitry.

The controller circuit 710 may include a processor such as a microprocessor, a digital signal processor, application specific integrated circuit (ASIC), microprocessor, or other type of processor, interpreting or executing instructions in software or firmware. The controller circuit 710 includes other circuits or sub-circuits to perform the functions described. These circuits may include software, hardware, firmware or any combination thereof. Multiple functions can be performed in one or more of the circuits as desired.

The controller circuit 710 includes an onset detection circuit 715. The onset detection circuit 715 can determine V-V intervals and A-A intervals using the sensed depolarization signal from the ventricle and the sensed depolarization signal from the atrium. The onset detection circuit 715 may detect an onset episode when detecting fast cardiac depolarizations. A fast cardiac depolarization is a cardiac depolarization that completes a depolarization interval that is less than a specified threshold interval value. In some examples, the onset detection circuit 715 detects an onset episode when M of N depolarizations are fast depolarizations (e.g., M=8 and N=10). The integers M and N can be programmable. The onset detection circuit 715 also identifies an onset cardiac depolarization in the atrium and an onset cardiac depolarization in the ventricle.

An example of a method of identifying an onset depolarization was described previously in regard to FIGS. 3 and 4. A threshold onset interval value is then determined based on a statistical metric (e.g., a standard deviation) and the onset depolarization is identified through comparison to the threshold onset interval. In some examples, the device 700 includes a storage circuit 725 (e.g., a memory) communicatively coupled to or integral to the controller circuit 710. To determine the threshold onset interval value, the storage circuit 725 stores a relationship between the statistical metric and threshold onset interval as a look-up table of threshold onset interval values. The onset detection circuit 715 determines the threshold onset value from the look-up table using the calculated statistical metric.

The controller circuit 710 also includes a classification circuit 720 to classify the detected onset of tachyarrhythmia. In some examples, the classification circuit 720 classifies the detected onset episode as cardiac signals are sensed (e.g., in real time). In some examples, the controller circuit 710 may store a segment of the atrial depolarization signal and a segment of the ventricular depolarization signal using the storage circuit 725 when the onset episode is detected by the onset detection circuit 715 (e.g., detection of onset triggers the storage of electrograms). The classification circuit 720 can then classify the onset episode using the stored signal segments when the onset is detected.

According to some examples, the classification circuit 720 classifies the onset episode as SVT when the V-V intervals differ from the A-A intervals by less than a specified interval threshold during the onset episode, the onset episode is initiated in the atrium, and the number of atrial depolarizations is greater than or equal to the number of ventricular depolarizations during the onset episode.

Because the V-V intervals differ from the A-A intervals by less than a specified interval threshold during the onset episode, the number of atrial depolarizations will differ from the number of ventricular depolarizations, if at all, by typically one or two depolarizations during an episode of SVT. An example of SVT detection was described previously in regard to FIG. 5.

In some examples, the classification circuit 720 classifies the onset episode as VT when the V-V intervals differ from the A-A intervals by less than a specified interval threshold during the onset episode, the onset episode is initiated in the ventricle, and the number of ventricular depolarizations is greater than the number of atrial depolarizations during the onset episode. Again, because the V-V intervals differ from the A-A intervals by less than a specified interval threshold, the number of ventricular events will differ from the number of atrial events by typically one or two during the detected onset episode. An example of VT detection was described previously in regard to FIG. 6.

According to some examples, the onset detection circuit 715 can detect a premature ventricular contraction (PVC). Detecting PVCs is helpful in classifying a tachyarrhythmia. In some examples, the classification circuit 720 uses the presence of PVCs or the absence of PVCs at the start of an onset of a tachyarrhythmia episode to classify the tachyarrhythmia.

In some examples, when the onset depolarizations are identified, the classification circuit 720 determines that the onset is initiated in the atrium when the atrial onset depolarization occurs within a specified time duration before the ventricular onset depolarization and no PVCs are detected near the identified ventricular onset depolarization. In this case the classification circuit 720 classifies the onset as SVT. The time duration (e.g., 750 milliseconds) can be a programmable parameter.

In some examples, the classification circuit 720 classifies the onset as VT when the V-V intervals and the A-A intervals differ by less than a specified interval threshold during the onset episode, the onset episode begins in the ventricle, the number of ventricular depolarizations is greater than the number of atrial depolarizations during the onset episode, and a PVC is detected near a ventricular depolarization designated as start of the onset episode. FIG. 6 shows an example of VT with a PVC occurring near the beginning of the onset episode.

To identify a PVC, in some examples the onset detection circuit 715 labels or otherwise identifies two ventricular depolarizations that occur, without an intervening atrial depolarization or beat, within N beats of the designated ventricular onset depolarization, where N can be a programmable integer. The onset detection circuit 715 may provide an indication that a PVC has occurred when detecting less than two atrial beats during two ventricular depolarizations following the two identified ventricular depolarizations.

In another example of detecting a PVC, the onset detection circuit 715 may indicate that a PVC has occurred when detecting an atrio-ventricular (AV) interval that is less than a specified threshold AV interval within N cardiac cycles of the ventricular onset depolarization.

To improve specificity of the tachyarrhythmia classification, in some examples the onset detection circuit 715 counts the number of depolarizations during the onset episode until the onset is classified. In certain examples, the onset detection circuit 715 counts both the number of depolarizations in the ventricle and in the atrium until the onset episode is classified. The count or counts are restarted if a new onset episode is detected before the onset episode is classified.

A complication to identifying the correct onset depolarization, and therefore identifying the correct heart chamber of origin, can occur if there are multiple candidate depolarizations that may be the onset depolarization. The correct onset interval can be identified by "pruning" of the candidate depolarization intervals.

As explained above in regard to FIG. 3, the onset depolarization may be identified by the onset detection circuit 715 as the first candidate depolarization that completes an interval less than the determined threshold onset interval, and at least X of the next Y intervals that follow the candidate depolarization are also less than the threshold onset interval. The onset detection circuit 715 may identify more than one candidate onset depolarization within the Y beats as the onset interval or onset depolarization.

Figure 8:
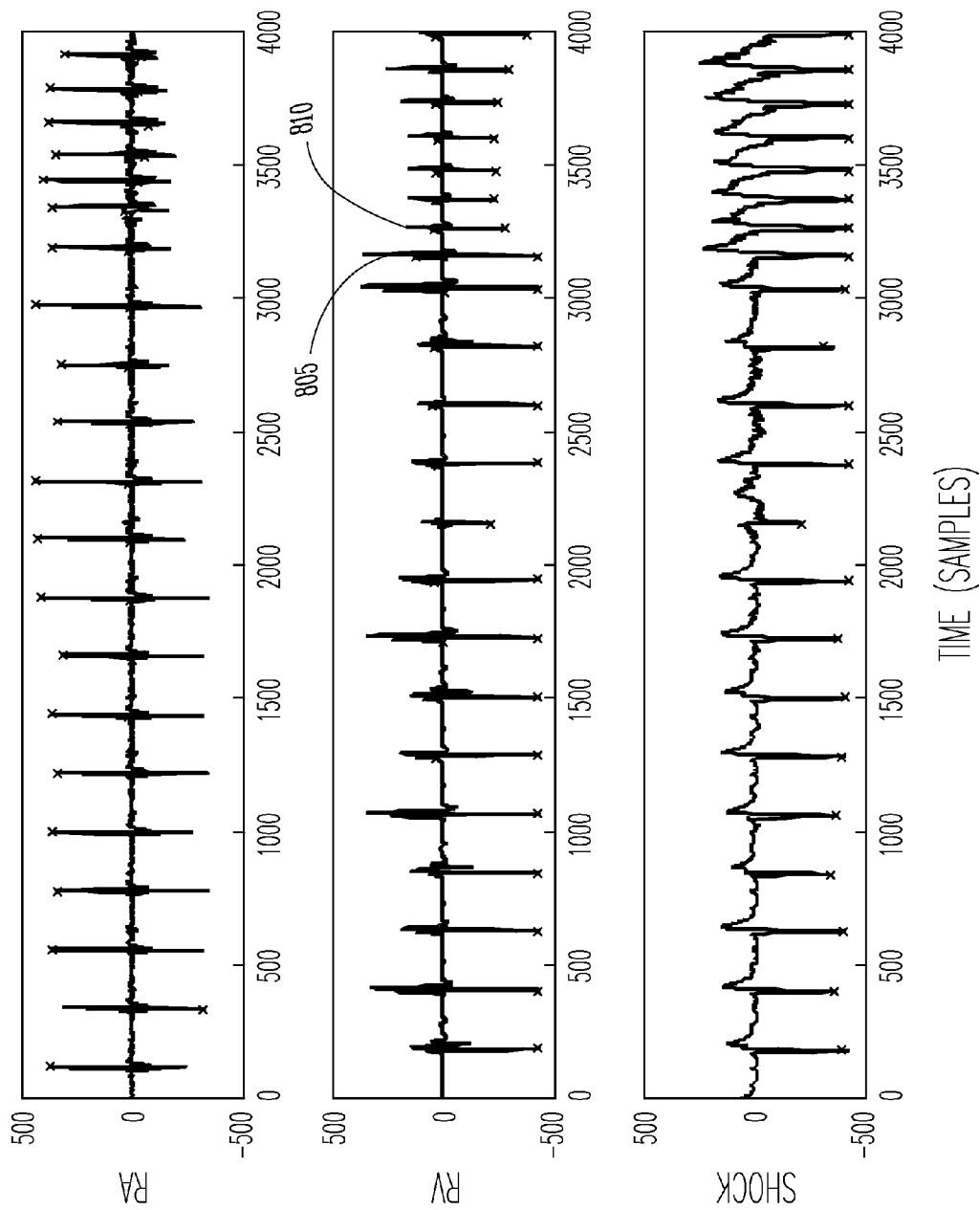
FIG. 8 shows an example of electrograms for an onset episode of tachyarrhythmia with multiple candidate onset depolarizations or intervals.

FIG. 8 shows an example of electrograms for an onset episode of tachyarrhythmia with multiple candidate onset depolarizations or intervals. The candidate depolarizations 805, 810 occur in the right ventricle (RV). To select the correct onset depolarization, the onset detection circuit 715 may select the first identified onset interval as the confirmed onset interval when the candidate onset intervals are consecutive. The onset detection circuit 715 may select the second identified onset interval as the confirmed onset interval when the candidate onset intervals are non-consecutive. Because the depolarizations shown in the Figure are consecutive, depolarization 805 is chosen as the depolarization that initiates the onset.

Figure 9:
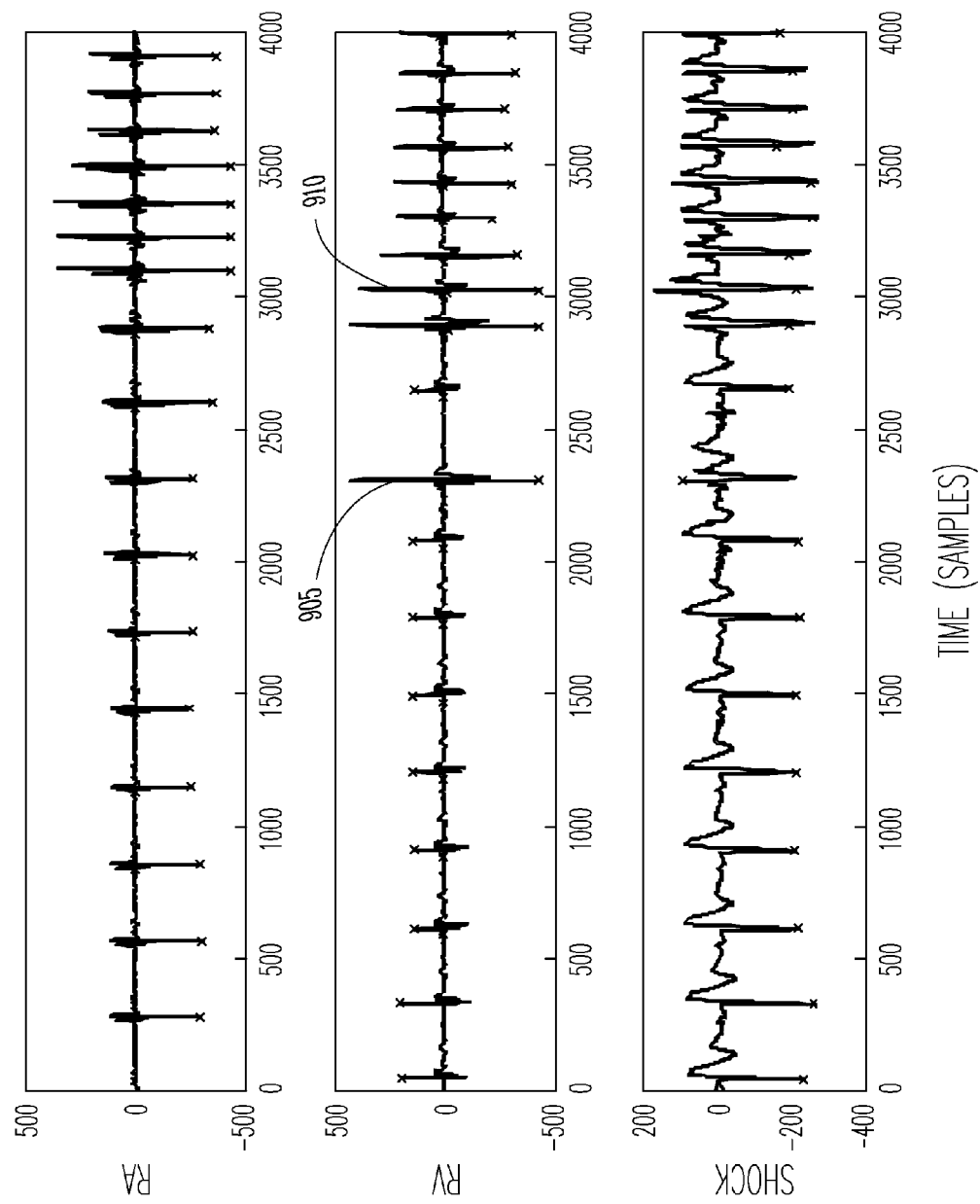
FIG. 9 shows another example of electrograms for an onset episode of tachyarrhythmia with multiple candidate onset depolarizations or intervals.

FIG. 9 shows another example of electrograms for an onset episode of tachyarrhythmia with multiple candidate onset depolarizations or intervals. The candidate depolarizations 905, 910 are non-consecutive and depolarization 910 is chosen as the onset depolarization.

When the onset episode is classified, the classification circuit 720 provides the classification to a user or process. In some examples, the process is a process executing on the controller circuit 710. In some examples, the device 700 includes a therapy circuit to provide one or more of anti-tachyarrhythmia pacing (ATP) therapy or high-energy defibrillation/cardioversion shock therapy to the subject. Upon receiving the classification of the onset episode, the controller circuit 710 may activate additional detection criteria, or may initiate delivery of anti-tachyarrhythmia therapy to the patient.

Anti-tachyarrhythmia therapy can result in perceived discomfort or acceleration of the tachyarrhythmia to higher rates that are poorly tolerated by the patient. For this reason, the controller circuit 710 may inhibit delivery of therapy if the classification is SVT. If the classification is VT, the controller circuit 710 may initiate delivery of ATP therapy if the VT includes a relatively slow tachyarrhythmia rate before resorting to shock therapy. If the classification is VT, the controller circuit 710 may directly initiate delivery of shock therapy.

In some examples, the process is executing on a remote device. The medical device 700 may include a communication circuit to wirelessly communicate information with a remote device. An approach to communications using an IMD can be found in U.S. Pat. No. 7,664,553, "Systems and Method for Enabling Communications with Implantable Medical Devices," filed Apr. 27, 2005, which is incorporated herein by reference in its entirety.

In some examples, the medical device 700 communicates a tachyarrhythmia classification to a remote device that includes an IMD programmer. In some examples, the device 700 communicates with the remote device via a third device (e.g., a repeater). In some examples, the remote device is part of an advanced patient management (APM) system, and includes a server connected to a computer network such as the internet for example.

The method of determining the heart chamber in which an arrhythmia began can be combined with other tachyarrhythmia detection enhancements. In some examples, the onset detection circuit 715 detects tachyarrhythmia when the ventricular heart rate exceeds the atrial heart rate (V rate>A rate). The onset detection circuit 715 may recurrently update an average ventricular contraction interval (V-V interval) and detects a tachyarrhythmia when the average ventricular depolarization rate exceeds an average atrial depolarization rate by more than a specified rate threshold value. Descriptions of systems and methods for classifying detected tachycardia based on average atrial and ventricular rates calculated from selected atrial and ventricular intervals is found in co-pending U.S. patent application Ser. No. 11/054,726, Elahi et al., entitled, "Method and Apparatus for Rate Accuracy Enhancement in Ventricular Tachycardia Detection," filed Feb. 10, 2005, which is incorporated herein by reference.

In another detection enhancement, the classification circuit 720 performs a morphology comparison of a sensed cardiac signal to a template of a known morphology (such as normal sinus rhythm) stored in memory. The classification circuit 720 can calculate a coefficient of correlation (e.g., a feature correlation coefficient or FCC) that is a measure of similarity between the sensed cardiac signal and the template. If the correlation coefficient indicates a high degree of similarity between the sensed cardiac signal and the template, the sensed rhythm is more likely to be supraventricular rhythm. For instance, if the calculated value of correlation exceeds a specified correlation threshold value, the classification circuit 720 classifies an onset episode as SVT.

Examples of methods to discriminate heart rhythms using analysis of the morphology of sensed cardiac signal can be found in Schwartz at al, "Cardiac Rhythm Management Systems and Methods Using Multiple Morphology Templates for Discriminating Between Rhythms," U.S. Pat. No. 7,031,764, filed Nov. 8, 2002 which is incorporated herein by reference in its entirety.

In another example, a template can be generated from a snapshot representative of one of the patient's normal supra-ventricular conducted beats. Cardiac signals are sensed from pacing leads (rate channel) and shock leads (shock channel). A fiducial point is determined from the signals sensed on the rate channels and is used to align signals sensed on the shock channels. A template for a patient is generated using the aligned shock channel signals. The template is representative of one of the patient's normal supra-ventricular conducted beats. Subsequently detected beats are then used to confirm that the generated template is representative of one of the patient's normal supra-ventricular conducted beats. Systems and methods for generating templates using a snapshot of the patient's normal supra-ventricular conducted beats are described in Kim et al., U.S. Pat. No. 6,708,058, entitled "Normal Cardiac Rhythm Template Generation System and Method," filed Apr. 30, 2001, which is incorporated herein by reference in its entirety.

In another example, a template of a patient's supraventricular rhythm is generated from characterizations performed while the heart is being paced. During the characterization, various pacing parameters are modified and the patient's supraventricular rhythm is characterized while the pacing parameters are modified. Systems and methods for generating a template to represent a patient's supraventricular rhythm are described in Bocek et al., U.S. Pat. No. 6,889,079, entitled "Method and System for Characterizing Supraventricular Rhythm During Cardiac Pacing," filed Apr. 12, 2002, which is incorporated herein by reference in its entirety.

Another tachyarrhythmia detection enhancement is rate stability. In some examples, the classification circuit 720 uses an assessment of heart rhythm stability to classify the arrhythmia when the onset detection circuit 715 detects a sudden increase in heart rate. Stability in the rhythm with a sudden onset tends to indicate VT while less stability or a more gradual onset may indicate SVT. Examples of methods and systems to detect arrhythmia and assess the stability of the rhythms are found in Gilkerson et al., U.S. Pat. No. 6,493,579, entitled "System and Method for Detection Enhancement Programming," filed Aug. 20, 1999, which is incorporated herein by reference in its entirety.

Figure 10:
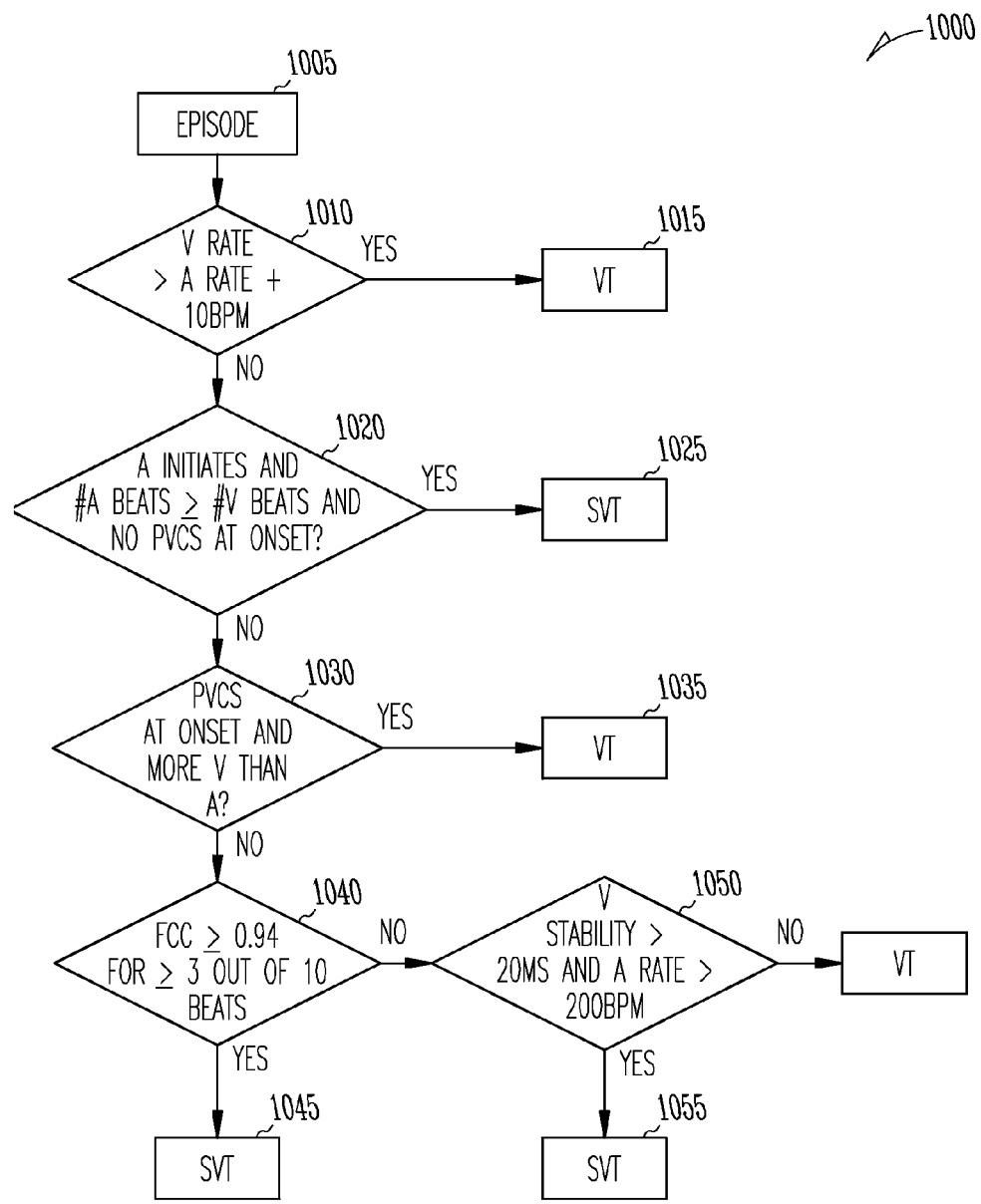
FIG. 10 shows a flow diagram of an example of a method that combines tachyarrhythmia detection enhancements.

FIG. 10 shows a flow diagram of an example of a method 1000 that combines tachyarrhythmia detection enhancements. At block 1005, an onset episode is detected by the onset detection circuit 715. At block 1010, the classification circuit 720 determines whether the V rate exceeds the A rate by a threshold rate value (e.g., 10 bpm). If the V rate does exceed the A rate by the threshold rate value, the classification circuit 720 classifies the episode as VT at block 1015. If the classification circuit 720 determines that the V rate does not exceed the A rate by the threshold rate value, the method 1000 continues at block 1020.

At block 1020, the classification circuit 720 determines whether the onset episode is initiated in the atrium and if the number of atrial depolarizations is greater than or equal to the number of ventricular depolarizations during the onset episode. If so, the classification circuit classifies the episode as SVT at block 1025. If the onset episode is not initiated in the atrium or if the number of atrial depolarizations is less than the number of ventricular depolarizations during the onset episode, the method continues to block 1030.

At block 1030, the classification circuit 720 determines whether the onset episode begins in the ventricle, whether the number of ventricular depolarizations is greater than the number of atrial depolarizations during the episode, and whether one or more PVCs are detected near the ventricular depolarization designated as start of the onset episode. If these conditions are satisfied, the classification circuit 720 classifies the onset episode as VT at block 1035. If the conditions of block 1030 are not satisfied, the method continues to block 1040.

At block 1040, the classification circuit 720 performs a morphology comparison of a sensed cardiac signal to a template. The morphology comparison may include calculation of an FCC and the stored template may be a representation of NSR. The classification circuit 720 determines whether the FCC satisfies a specified FCC threshold (e.g., FCC$\geq$0.94) for a specified number of X beats out of Y beats (e.g., 3 out of 10 beats). If the sensed cardiac signal sufficiently compares to the template of NSR, the classification circuit 720 classifies the onset episode as SVT at block 1045. If the conditions of block 1040 are not satisfied, the method continues to block 1050.

At block 1050, the classification circuit 720 determines a measure of stability of the ventricular rate. In some examples, if the variation in sensed ventricular depolarizations exceeds a threshold variation threshold value and the atrial rate exceeds a specified atrial rate threshold, the classification circuit 720 classifies the rate as SVT at block 1055. If the conditions of block 1050 are not satisfied, the classification circuit 720 classifies the episode as VT at block 1060.

Figure 11:
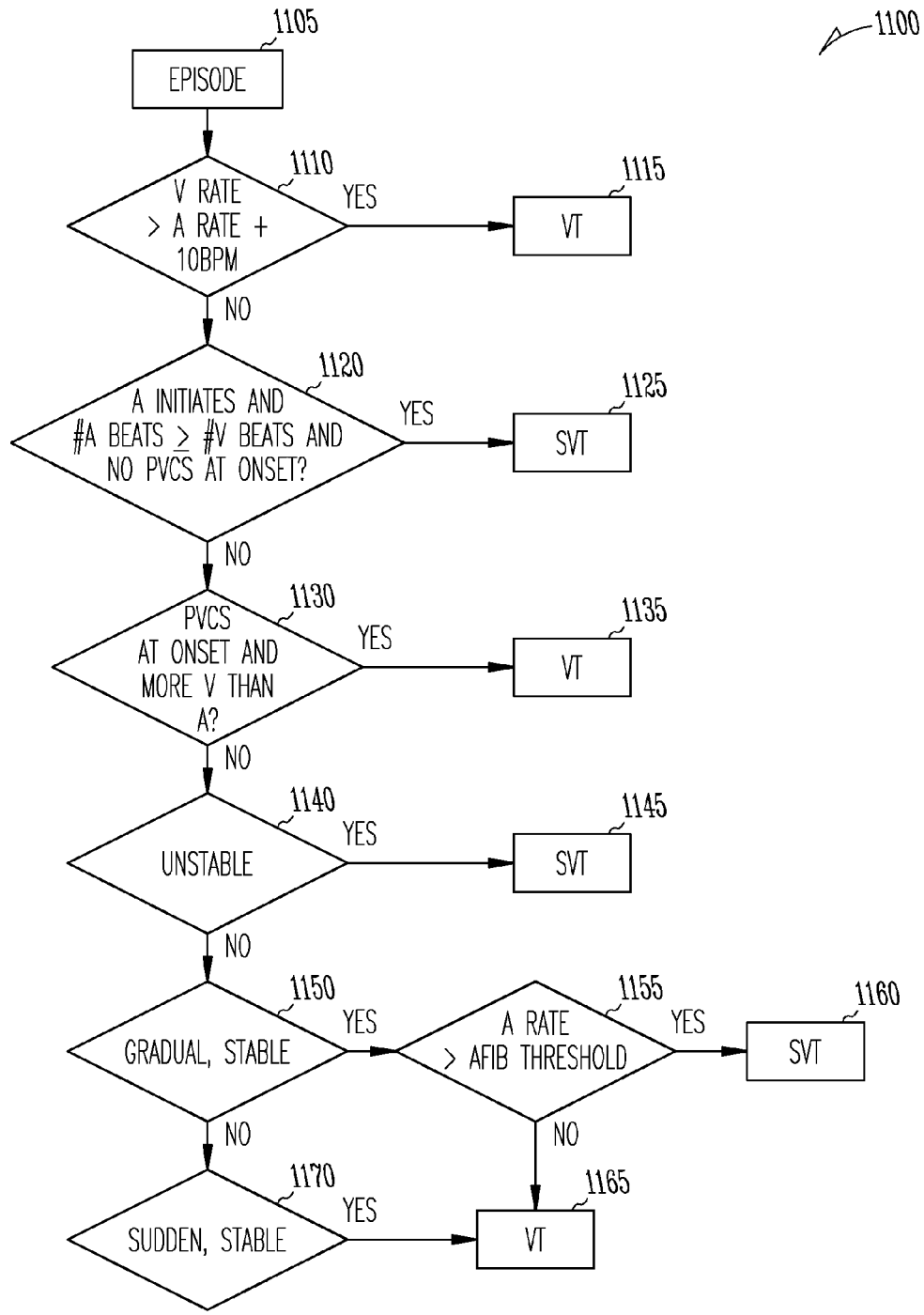
FIG. 11 shows a flow diagram of another example of a method that combines tachyarrhythmia detection enhancements.

FIG. 11 shows a flow diagram of another example of a method 1100 that combines tachyarrhythmia detection enhancements. At block 1105, an onset episode is detected by the onset detection circuit 715. At block 1110, the classification circuit 720 determines whether the V rate exceeds the A rate by a threshold rate value (e.g., 10 bpm). If the V rate does exceed the A rate by the threshold rate value, the classification circuit 720 classifies the episode as VT at block 1015. If the conditions of block 1110 are not satisfied, the method 1100 continues at block 1120.

At block 1120, the classification circuit 720 determines whether the onset episode is initiated in the atrium and if the number of atrial depolarizations is greater than or equal to the number of ventricular depolarizations during the onset episode. If these conditions are satisfied, the classification circuit classifies the episode as SVT at block 1125. If the conditions of block 1120 are not satisfied, the method continues to block 1130.

At block 1130, the classification circuit 720 determines whether the onset episode begins in the ventricle, whether the number of ventricular depolarizations is greater than the number of atrial depolarizations during the episode, and whether one or more PVCs are detected near the ventricular depolarization designated as start of the onset episode. If these conditions are satisfied, the classification circuit 720 classifies the onset episode as VT at block 1135. If the conditions of block 1030 are not satisfied, the method continues to block 1140.

At block 1140, the classification circuit 720 determines a measure of stability of V-V intervals. In some examples, the classification circuit 720 measures the differences between V-V intervals. If the V-V intervals are stable then the V-V intervals are uniform and the differences will approach zero. If the V-V intervals are unstable, then the calculated differences will be greater than zero. If the measured differences indicate that the rhythm during the detected episode is unstable, the classification circuit 720 classifies the episode as SVT at block 1145. If the classification circuit 720 determines that the rhythm is stable, the method continues at block 1150.

At block 1150, if the measured differences indicate that the rhythm during the detected episode is stable and the onset detection circuit 715 determined that an increase in heart rate was gradual rather than sudden, the method proceeds to 1155. At block 1155, if the A rate is less than a specified atrial fibrillation detection rate threshold, the classification circuit 720 classifies the episode as SVT at block 1160. If the A rate satisfies the atrial fibrillation detection rate threshold, the classification circuit 720 classifies the episode as VT at block 1165.

At block 1170, if the measured differences indicate that the rhythm during the detected episode is stable and the onset detection circuit 715 determined that an increase in heart rate was sudden rather than gradual, the classification circuit 720 classifies the episode as VT at block 1165.

Determining the heart chamber in which an arrhythmia began can be useful alone in classifying tachyarrhythmia or can be useful when combined with other tachyarrhythmia detection enhancements. As explained above, determining the chamber of the origin of the arrhythmia may be helpful when ventricular events occur about one-to-one with atrial events during a tachyarrhythmia. However, the techniques described herein are also useful in detecting and classifying tachyarrhythmia episodes that are not one-to-one.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
   an implantable cardiac signal sensing circuit, configured to provide a sensed depolarization signal from a ventricle and a sensed depolarization signal from an atrium; and
   a controller circuit communicatively coupled to the implantable cardiac signal sensing circuit, wherein the controller circuit includes:
   an onset detection circuit configured to:
      determine ventricular depolarization intervals (V-V intervals) and atrial depolarization intervals (A-A intervals);
      detect an onset episode that includes fast cardiac depolarizations; and
      identify an initiating onset depolarization in the onset episode; and
   a classification circuit configured to:
      classify the onset episode, when the V-V intervals differ from the A-A intervals by less than a specified interval threshold during the onset episode, as:
         supra-ventricular tachycardia (SVT) when the initiating onset depolarization is identified in the atrium and the number of atrial depolarizations is greater than or equal to the number of ventricular depolarizations during the onset episode; and
         ventricular tachycardia (VT) when the initiating onset depolarization is identified in the ventricle, the number of ventricular depolarizations is greater than the number of atrial depolarizations during the onset episode; and
      provide the classification to a user or process.

2. The apparatus of claim 1,
   wherein the onset detection circuit is configured to detect a premature ventricular contraction (PVC), and wherein the classification circuit is configured to classify
the onset as VT when:
the V-V intervals and the A-A intervals differ by less than
a specified interval threshold during the onset episode;
the onset episode begins in the ventricle;
the number of ventricular depolarizations is greater than
the number of atrial depolarizations during the onset
episode; and
a PVC is detected near a ventricular depolarization designated as start of the onset episode.

3. The apparatus of claim 1, wherein the onset detection circuit is configured to:
identify two ventricular depolarizations that occur, without an intervening atrial beat, within N beats of the designated ventricular onset depolarization, wherein N is an integer; and
provide an indication that a PVC has occurred when detecting less than two atrial depolarizations during two ventricular depolarizations following the two identified ventricular depolarizations.

4. The apparatus of claim 1, wherein the onset detection circuit is configured to provide an indication that a PVC has occurred when detecting an atrio-ventricular (AV) interval that is less than a specified threshold AV interval within N cardiac cycles of the ventricular onset depolarization, wherein N is an integer.

5. The apparatus of claim 1,
wherein the onset detection circuit is configured to identify an onset cardiac depolarization in the atrium and an onset cardiac depolarization in the ventricle, and
wherein the classification circuit is configured to determine that the onset is initiated in the atrium when the atrial onset depolarization occurs before the ventricular onset depolarization and no PVCs are detected near the identified ventricular onset depolarization.

6. The apparatus of claim 1, wherein the onset detection circuit is configured to:
determine a threshold onset interval value using sensed cardiac depolarizations;
identify a depolarization as a candidate onset depolarization if the depolarization completes an interval less than the threshold onset interval value; and
classify the candidate onset depolarization as an initiating onset depolarization when X depolarization intervals of the next Y cardiac depolarizations following the candidate onset depolarization are less than the threshold onset interval value, wherein X and Y are positive integers and X is less than Y.

7. The apparatus of claim 6, wherein the onset detection circuit is configured to:
calculate a statistical metric of a depolarization interval change measured over a specified number of previous depolarization intervals; and
determine the threshold onset interval value using the statistical metric.

8. The apparatus of claim 7, including a storage circuit communicatively coupled to the controller and configured to store a look-up table of threshold onset interval values, and wherein the onset detection circuit is configured to determine the threshold onset value from the look-up table using the calculated statistical metric.

9. The apparatus of claim 6, wherein the onset detection circuit is configured to:
identify more than one candidate onset interval within the Y beats as the onset interval;
select the first identified onset interval as the confirmed onset interval when the candidate onset intervals are consecutive; and
select the second identified onset interval as the confirmed onset interval when the candidate onset intervals are non-consecutive.

10. The apparatus of claim 1, including a storage circuit communicatively coupled to, or integral to, the controller circuit,
wherein the controller circuit is configured to store a segment of the atrial depolarization signal and a segment of the ventricular depolarization signal using the storage circuit when the onset episode is detected, and
wherein the classification circuit is configured to classify the onset episode using the stored signal segments when the onset is detected.

11. The apparatus of claim 1, wherein the onset detection circuit is configured to:
count the number of depolarizations during the onset episode until the onset is classified; and
restart the count if a new onset episode is detected before the before the onset episode is classified.

12. A method comprising:
sensing cardiac depolarizations in an atrium and in a ventricle of a heart of a subject using an implantable medical device (IMD);
detecting an onset episode that includes fast cardiac depolarizations;
determining that ventricular depolarization intervals (V-V intervals) and atrial depolarization intervals (A-A intervals) differ by less than a specified interval threshold during the onset episode;
identify an initiating onset depolarization in the onset episode;
classifying the onset episode as supra-ventricular tachycardia (SVT) when the initiating onset depolarization is identified in the atrium and the number of atrial depolarizations is greater than or equal to the number of ventricular depolarizations during the onset episode;
classifying the onset episode as ventricular tachycardia (VT) when the initiating onset depolarization is identified in the ventricle and the number of ventricular depolarizations is greater than the number of atrial depolarizations during the onset episode; and
providing the classification to a user or process.

13. The method of claim 12, wherein classifying the onset includes classifying the onset episode as VT when:
determining that the V-V intervals differ from A-A intervals by less than the specified interval threshold during the onset episode;
determining that the onset episode begins in the ventricle;
determining that the number of ventricular depolarizations is greater than the number of atrial depolarizations during the onset episode; and
detecting a premature ventricular contraction (PVC) near a ventricular depolarization designated as start of the onset episode.

14. The method of claim 13, wherein detecting a PVC includes:
identifying two ventricular depolarizations, that occur without an intervening atrial depolarization, within N cardiac cycles of the ventricular onset depolarization, wherein N is an integer; and
deeming a PVC has occurred when detecting less than two atrial depolarizations during two ventricular depolarizations following the two identified ventricular depolarizations.

15. The method of claim 13, wherein detecting a PVC includes detecting an atrio-ventricular (AV) interval that is less than a specified threshold AV interval within N cardiac cycles of the ventricular onset depolarization, wherein N is an integer.

16. The method of claim 12, including:
   identifying an onset cardiac depolarization in the atrium and an onset cardiac depolarization in the ventricle; and
   deeming that the onset is initiated in the atrium when the identified atrial onset depolarization occurs within a specified time duration before the identified ventricular onset depolarization and no PVCs are detected near the identified ventricular onset depolarization.

17. The method of claim 12, wherein detecting the onset of fast cardiac depolarizations includes:
   determining a threshold onset interval value;
   identifying a depolarization as a candidate onset depolarization if the depolarization completes an interval less than the threshold onset interval value; and
   confirming the candidate onset depolarization as an initiating onset interval when X depolarization intervals of the next Y cardiac depolarizations following the candidate onset depolarization complete intervals less than the threshold onset interval value, wherein X and Y are positive integers and X is less than Y.

18. The method of claim 17, wherein determining a threshold onset interval value includes determining the threshold onset interval value by applying a statistical metric to a depolarization interval change measured over a specified number of previous depolarization intervals.

19. The method of claim 17, wherein, when identifying more than one candidate onset interval within the Y beats as the onset interval, confirming the onset interval includes:
   selecting the first identified onset interval as the confirmed onset interval when the candidate onset intervals are consecutive; and
   selecting the second identified onset interval as the confirmed onset interval when the candidate onset intervals are non-consecutive.

20. The method of claim 12, including classifying the onset episode as one of VT or SVT when a determined ventricular depolarization rate differs from a determined atrial depolarization rate by less than a specified rate threshold.

* * * * *